United States Patent [19]

Holtkamp, Sr.

[11] Patent Number: Plant 6,931

[45] Date of Patent: Jul. 18, 1989

[54] AFRICAN VIOLET PLANT NAMED IMPROVED MARYLAND

[76] Inventor: Reinhold Holtkamp, Sr., Werther Strasse 112, D4294 Isselburg, Fed. Rep. of Germany

[21] Appl. No.: 192,681

[22] Filed: May 10, 1988

[51] Int. Cl.[4] ..... A01H 5/00

[52] U.S. Cl. ..... Plt./69

[58] Field of Search ..... Plt./69

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A new and distinct cultivar of African violet named Improved Maryland characterized by its single to semi-double, violet-blue flowers with frilled edges and somewhat darker center; strong, upright flowers stems that curve slightly toward the center to form a compact bouquet above the leaves; medium green oval to heart-shaped, slightly serrated leaves; profuse flowering, vigorous growth habit, flowering 10–11 weeks after potting, and its long lasting and non-dropping flowers.

1 Drawing Sheet

The present invention comprises a new and distinct cultivar of African violet plant, botanically known as *Saintpaulia ionantha,* and hereinafter referred to by the cultivar name Improved Maryland.

The new cultivar was referred to during the breeding and selection process by the designation H 81/4 and is a product of a planned breeding program. The basic objective of the breeding program was to create a new African violet cultivar improving certain characteristics of the cultivar Maryland, disclosed in my U.S. Plant Pat. No. 4,216 granted in 1978. The new cultivar was originated from a cross made by me in the controlled breeding program in Haffen, Federal Republic of Germany. The female, or seed parent was a cultivar designated C 81/1. The male, or pollen parent was a cultivar designated B 219/3.

Improved Maryland was discovered and selected by me in as a flowering plant within the progeny of the stated cross in a controlled environment in Haffen, West Germany. Asexual reproduction of the new cultivar by leaf cuttings, as performed by me at Haffen, West Germany, has demonstrated that the combination of characteristics as herein disclosed for the new cultivar are firmly fixed and retained through successive generations of asexual reproduction.

Improved Maryland has not been observed under all possible environmental conditions. The phenotype may vary significantly with variations in environment such as temperature, light intensity and day length. The following observations, measurements and values describe the new cultivar as grown in a 10 cm pot in Haffen, West Germany and Nashville, Tenn. under greenhouse conditions which closely approximate those generally used in commercial practice.

The following traits have been repeatedly observed and are determined to be basic characteristics of Improved Maryland, which in combination distinguish this African violet as a new and distinct cultivar:

(1) Strong, upright flower stems curving slightly toward the center.
(2) Single to semi-double violet-blue flowers with frilled edges.
(3) Each plant carries 6–8 and more upright flower stems each of which carries 7–9 and more flowers.
(4) Long lasting, non-dropping flowers.
(5) Vigorous grower.

(6) Plant saleable 10 to 11 weeks after potting.
(7) Seed capsules push slightly through.
(8) Oval to heart-shaped, slightly serrated, medium green leaves.
(9) After maturity the flowers dry off, and remain on the peduncle without becoming infected by botrytis.

The new cultivar is most similar to, and was specifically intended to improve upon the characteristics of, my previously patented cultivar, Maryland. In comparison to Maryland which had star-shaped flowers, the new cultivar is principally distinguished by its single to semi-double, violet-shaped flowers, somewhat smaller flowers and improved flowering habit. The new cultivar is also similar to Acadia whose flower color and flower shape are similar to Improved Maryland. However, Acadia has semi-double to double flowers, whereas Improved Maryland has single to semi-double flowers. Other differences between Acadia and Improved Maryland are the larger, flatter and more oval leaves of Improved Maryland.

The accompanying color photographic drawing shows a typical specimen plant of the new cultivar. The colors appearing in the photograph are as true as possible with color illustrations of this type.

In the following description, color references are made to The Royal Horticultural Society Colour Chart (R.H.S.), except where general colors of ordinary significance are referred to. Color values were taken under natural sunlight conditions at approximately 2 p.m. in Nashville, Tenn.

Botanical classification: *Saintpaulia ionantha,* Ramat, c.v. Improved Maryland.

Parentage: Male parent: B 219/3. Female parent: C 81/1.

Propagation: The new cultivar holds its distinguishing characteristics through successive propagations by leaf cuttings.

Plant: From 8 cm to 10 cm tall when grown in pots, and approximately 25–28 cm in diameter when fully grown.

*Leaves.*—General form: Oval to heart-shaped. Diameter: 60–75 mm wide and 70–85 mm long. Texture: Leatherlike. Aspect: Hairy, slightly shiny, slightly serrated. Veins: Upperside: well visible; underside; very well pronounced, light green, shiny. Color (upperside): Yellow-Green Group 147 between A and B. Color (underside): Greyed-Green Group 194 D. Petiole: Strong upright, green with purplish brown touch, hairy.

*Flowers.*—Buds: Bell-shaped, 8–9 mm just before opening, light bluish green. Sepals: Five (5). Color: Brownish green. Calyx: Shape: Funnel-shaped. Aspect: Spear-shaped, hairy. Peduncle: Character: Strong upright, hairy. Color: Brownish green. Individual flowers: Size: 35–40 mm. Shape: Single violet-shaped (3 large, 2 small petals), to semi-double having up to 5 more petals; frilled edges. Color (upperside): Violet-Blue Group 93 C. Under cooler temperatures and more intensive lighting, the blue tends to intensify. Color (underside): Violet-Blue Group 88 D. Borne: Each flower stem carries 7–9 and more flowers on strong, upright peduncle that are free standing above the leaves, thereby forming a compact bouquet. Flowering habit: Flowers 10–11 weeks after potting.

*Reproductive organs.*—Stamens: Two (2) to three (3). Anthers: 2–3 composed of 4–6 anther cells, seed capsule pushes slightly through. Filaments: Yellowish green, with blue touch on edge, 4 mm long. Pollen color: Yellow Group 7. Styles: 7–8 mm long, purplish blue, base of ovary light green and hairy.

*Roots.*—Normally developed, white when young, turning slightly brownish when older.

Disease resistance: Good.

General observations: Improved Maryland is a very attractive, vigorous grower with medium green, oval to heart-shaped, slightly serrated leaves. A tight bouquet of flowers free standing above the leaves develops after approximately 10–11 weeks. Each of the 6–8 and more strong flower stems carries 7–9 and more single to semi-double (having up to five additional petals) violet-blue flowers with frilled edges. The center of the flower is somewhat darker and radiates into the two small petals. The two to three bright yellow anthers are sometimes not visible due to the semi-double flower shape. The flowers are long-lasting and non-dropping and the seed capsules push slightly through.

I claim:

1. A new and distinct cultivar of African violet named Improved Maryland, as described and illustrated, and particularly characterized by its single to semi-double, violet-blue flowers with frilled edges and somewhat darker center; strong, upright flowers stems that curve slightly toward the center to form a compact bouquet above the leaves; medium green oval to heart-shaped, slightly serrated leaves; profuse flowering, vigorous growth habit, flowering 10–11 weeks after potting, and its long lasting and non-dropping flowers.

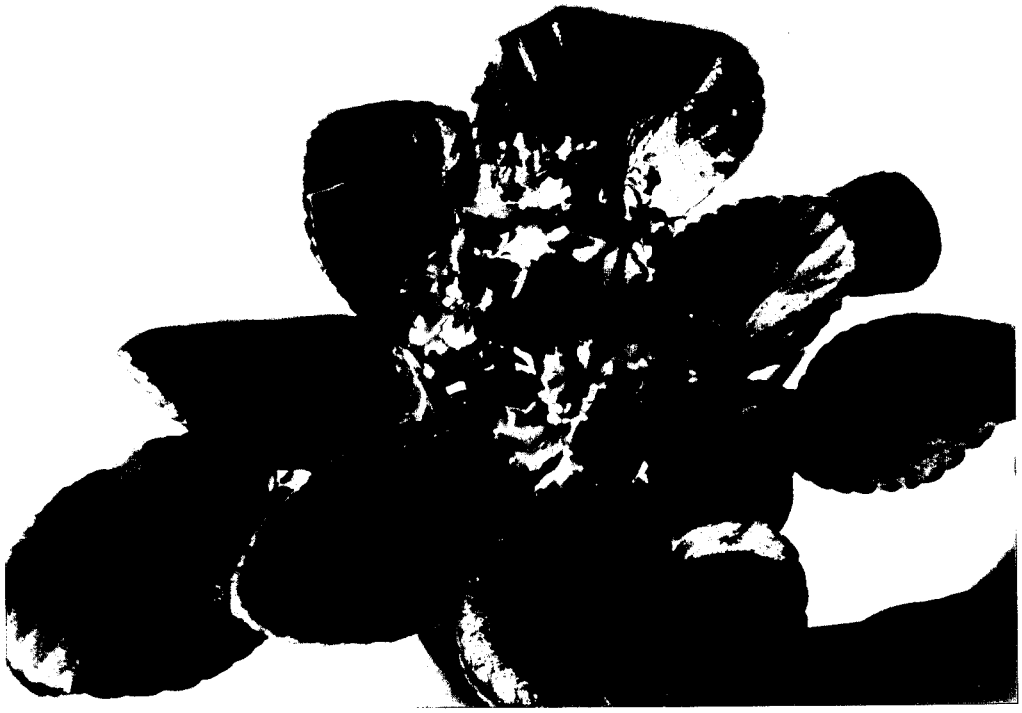

* * * * *